(12) United States Patent
Contolini et al.

(10) Patent No.: US 10,891,394 B2
(45) Date of Patent: Jan. 12, 2021

(54) SYSTEM AND METHOD FOR IDENTIFYING AND AUTHENTICATING A USER OF A MEDICAL DEVICE, AND CONTROLLING ACCESS TO PATIENT DATA GENERATED BY THE MEDICAL DEVICE

(71) Applicant: Karl Storz Imaging, Inc., Goleta, CA (US)

(72) Inventors: Matteo Contolini, Goleta, CA (US); Juri Baumberger, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 242 days.

(21) Appl. No.: 15/907,919

(22) Filed: Feb. 28, 2018

(65) Prior Publication Data
US 2019/0266344 A1 Aug. 29, 2019

(51) Int. Cl.
*G06F 21/62* (2013.01)
*G16H 10/60* (2018.01)
(Continued)

(52) U.S. Cl.
CPC .......... *G06F 21/6245* (2013.01); *A61B 5/067* (2013.01); *A61B 5/117* (2013.01); *G06F 21/32* (2013.01); *G06K 9/00885* (2013.01); *G16H 10/60* (2018.01); *G16H 40/63* (2018.01); *H04L 63/102* (2013.01); *H04L 67/306* (2013.01); *A61B 5/1102* (2013.01); *G06K 2009/00932* (2013.01)

(58) Field of Classification Search
CPC ... G06F 21/6245; G06F 21/32; H04L 63/102; H04L 67/306; G16H 10/60; G16H 10/40–63; A61B 5/067; A61B 5/117
See application file for complete search history.

(56) References Cited

U.S. PATENT DOCUMENTS 6,425,861 B1 * 7/2002 Haberland ........... A61B 5/0002
600/300
6,643,531 B1 * 11/2003 Katarow .............. A61B 5/1172
600/323
(Continued)

FOREIGN PATENT DOCUMENTS

EP 2679140 A1 1/2014

OTHER PUBLICATIONS

Extended European Search Report Application No. 19159840.8 Search Completed: Jul. 5, 2019; dated Jul. 7, 2019 13 Pages.
(Continued)

*Primary Examiner* — Saleh Najjar
*Assistant Examiner* — Devin E Almeida
(74) *Attorney, Agent, or Firm* — Whitmyer IP Group LLC

(57) ABSTRACT

A system includes a medical device and an authenticator. The medical device has a medical sensor configured to generate patient data indicative of a sensed physiological characteristic of a patient. The authenticator has at least one biometric sensor configured to generate at least one biometric signal indicative of at least one biometric characteristic of a user of the medical device. The authenticator is configured to (i) identify and authenticate a user of the medical device, (ii) protect patient data generated by the medical sensor of the medical device using a user ID unique to the identified user, and (iii) save the protected patient data to a memory.

26 Claims, 4 Drawing Sheets

(51) Int. Cl.
  *A61B 5/06* (2006.01)
  *A61B 5/117* (2016.01)
  *G06F 21/32* (2013.01)
  *G06K 9/00* (2006.01)
  *H04L 29/06* (2006.01)
  *H04L 29/08* (2006.01)
  *G16H 40/63* (2018.01)
  *A61B 5/11* (2006.01)

(56) References Cited

U.S. PATENT DOCUMENTS

| | | | | |
|---|---|---|---|---|
| 8,679,012 | B1* | 3/2014 | Kayyali | A61B 5/0002 600/301 |
| 2003/0043265 | A1* | 3/2003 | Watai | A61B 1/00045 348/74 |
| 2009/0005652 | A1* | 1/2009 | Kurtz | A61B 5/00 600/300 |
| 2013/0312066 | A1* | 11/2013 | Suarez | G16H 40/67 726/4 |
| 2014/0002624 | A1* | 1/2014 | Nemoto | A61B 1/00039 348/65 |
| 2014/0118518 | A1* | 5/2014 | Fructus | A61B 1/00059 348/65 |
| 2014/0267658 | A1* | 9/2014 | Speier | H04N 7/181 348/72 |
| 2016/0119305 | A1* | 4/2016 | Panchura | H04L 63/0861 726/5 |
| 2018/0130473 | A1* | 5/2018 | Odinak | G10L 17/20 |

OTHER PUBLICATIONS

Jesse Kyle Earisman et al.: "Worcester Polytechnic Institute Digital WPI Passive Biometric Authentication via Head Mounted Display using Ballistocardiography Repository Citation", Mar. 20, 2017, Retrieved from the Internet on Jul. 17, 2019 URL:https://digitalcommons.wpi.edu/cgi/viewcontent.cgi?article=5057&context=mqp-all.

L. Wang et al.: "Infrared imaging of hand vein patterns for biometric purposes", IET Computer Vision, vol. 1, No. 3, Dec. 1, 2007, Michael Faraday House, Six Hills Way, Stevenage, Herts, United Kingdom pp. 113-122.

Thomas Neubauer et al,: "A methodology for the pseudonymization of medical date" International Journal of Medical Informatics, Elsevier Scientific Publishers, Shannon, IR, vol. 80, No. 3, Oct. 19, 2010 pp. 190-204.

Hernandez, Javier, et al. BioInsights: Extracting Personal Data from "Still" Wearable Motion Sensors, May 26, 2015, Retrieved from the Internet: http://affect.media.mit.edu/pdfs/15.Hernandez.McDuff.Picard-BSN.pdf (retrieved on Feb. 28, 2018.).

Mearian, Lucas. "Hospital turns to palm reading to ID patients" The infrared palm scanner thwarts ID theft, Jun. 16, 2011, Retrieved from the Internet: https://www.computerworld.com/article/2509052/healthcare-it/hospital-turns-to-palm-reading-to-id-patients.html (retrieved on Feb. 28, 2018.).

M. Watanabe, et. al. "Palm vein authentication technology and its applications" Proceedings of the Biometric Consortium Conference, Sep. 19-21, 2005, Hyatt Regency Crystal City, Arlington, VA, USA. 2 Pages.

Greenemeier, Larry. "Palm-Reading Devices Get Smart about Security" A new biometrics system uses the blood network in the palms of your hand to ID individuals, Jun. 24, 2008, Retrieved from the Internet: https://www.scientificamerican.com/article/palm-reading-devices/ (retrieved on Feb. 28, 2018.).

I. Sarkar, et.al. "Palm Vein Authentication System: A Review" International Journal of Control and Automation, vol. 3, No. 1, Mar. 2010. pp. 27-34.

* cited by examiner

SYSTEM AND METHOD FOR IDENTIFYING AND AUTHENTICATING A USER OF A MEDICAL DEVICE, AND CONTROLLING ACCESS TO PATIENT DATA GENERATED BY THE MEDICAL DEVICE

TECHNICAL FIELD

The present disclosure generally relates to a system and method for identifying and authenticating a user of a medical device, and controlling access to patient data generated by the medical device. The present disclosure more particularly relates to a system and method for identifying and authenticating a user of a medical device when patient data is generated and stored by the medical device, and when the stored patient data is extracted from the medical device, and for controlling access to the stored patient data without negatively affecting workflow and/or preventing use of the medical device in an emergency situation.

BACKGROUND

There are many known medical devices that at least temporarily store patient data (pictures, videos, etc.). Often times, the patient data can be extracted from the medical device by anyone having physical access to the medical device. This creates a risk that personally identifiable information (PII) and/or protected health information (PHI) included in or associated with the patient data could be extracted from the medical device by unauthorized personnel, resulting in a violation of one or more health information privacy laws (e.g., HIPAA).

Known solutions for protecting patient data saved to a medical device include requiring user login (e.g., via entry of a username and password) prior to use of the medical device, and requiring user logout when use of the medical device is complete. Such solutions can be problematic in that they can highly degrade the user experience. For example, the need to enter a username and password can negatively affect workflow and/or force the medical professional to break sterility. Such solutions can also pose a hazard to patients. For example, in an emergency, the medical device could be rendered inoperable if the medical professional does not have, or forgot, their username and/or password. Such solutions also suffer from vulnerability to break-in. For example, there is a risk that a username and password could be discovered (e.g., by covert observation, hacking, etc.) and used by an unauthorized user to extract patient data from the medical device. There is also a risk that an authorized medical professional could mistakenly forget to logout when use of the medical device is complete, thereby allowing an unauthorized user to extract patient data from the medical device.

It is also known that a biometric sensor can be used to identify a user based on a detected physiological or behavioral characteristic of the user (e.g., face, fingerprint, iris, retinal, voice, etc.) (hereinafter a "biometric characteristic"). Biometric sensors can be advantageous in that they are relatively difficult to circumvent, since a user's biometric characteristics typically cannot be transferred to another user. However, biometric sensors may be disfavored by users who view them as being overly intrusive from a privacy standpoint. Also, in the context of medical devices, the intended user is a medical professional who will typically be wearing latex gloves, a protective face mask, and/or protective glasses. Latex gloves can make it difficult or impossible to accurately detect fingerprints, a face mask can make it difficult or impossible to accurately detect a user's face and voice, and protective glasses can make it difficult or impossible to properly scan a user's iris and retina.

Biometric sensors that identify a user based on a detected palm vein pattern (sometimes referred to hereinafter as "palm vein pattern sensors") can be especially difficult to circumvent due the uniqueness and complexity of vein patterns of the palm, and the fact that vein patterns are subcutaneous (i.e., beneath the skin). Palm vein pattern sensors are typically designed to detect a vein pattern of a palm that is held at a distance (e.g., a few inches) away therefrom. This allows the palm vein pattern sensor to be contactless and thus hygienic for use in public areas.

Recently, biometric sensors have been developed that identify a user based on a detected ballistocardiography (BCG) signal. Such biometric sensors (sometimes referred to hereinafter as "BCG sensors") provide a measure of the repetitive, subtle motions of a user's body caused by the user's beating heart and the corresponding shifts to the center of mass of the user's body due to the blood flowing through the user's body. BCG signals are unique for each individual person, and thus can be used to identify a user. The use of BCG sensors is prevented in many contexts due to the fact that a person must be still for a certain amount of time (e.g., 10 seconds) in order for the BCG sensor to obtain an accurate reading. Also, known experimental work shows that the body posture can highly influence the quality of the data generated by BCG sensors. In order to obtain an accurate identification, several statistical (or mathematical) models of the data are typically needed for each posture. The identification usually consists of two steps: (i) guessing the person's posture; and (ii) applying the statistical model for that posture to identify the particular user. Each of these steps can lead to misclassifications.

Another problem common to many known biometric sensors is that they require a user to pre-enroll before first use. Pre-enrollment can involve the user providing identifying biographic information (e.g., name) together with one or more samples of the biometric characteristic sensed by the biometric sensor (e.g., face, fingerprint, iris, retinal, voice, etc.). In the context of medical devices, the pre-enrollment steps required by many known biometric sensors can be problematic in that they can negatively affect workflow, and can pose a hazard to patients during an emergency situation by rendering the medical device inoperable while the user performs the pre-enrollment steps.

Aspects of the present invention are directed to these and other problems.

SUMMARY

According to an aspect of the present invention, a system is provided that includes a medical device and an authenticator. The medical device has a medical sensor configured to generate patient data indicative of a sensed physiological characteristic of a patient. The authenticator has at least one biometric sensor configured to generate at least one biometric signal indicative of at least one biometric characteristic of a user of the medical device. The authenticator is configured to (i) identify and authenticate a user of the medical device, (ii) protect patient data generated by the medical sensor of the medical device using a user ID unique to the identified user, and (iii) save the protected patient data to a memory.

According to another aspect of the present invention, a method is provided that includes the steps of: generating patient data using a medical device, the patient data indicative of a sensed physiological characteristic of a patient; identifying and authenticating a user of the medical device based on at least one biometric signal generated by at least one biometric sensor; protecting patient data generated by the medical device using a user ID unique to the user identified during the identifying and authenticating step; and saving the protected patient data to a memory.

In addition to, or as an alternative to, one or more of the features described above, further aspects of the present invention can include one or more of the following features, individually or in combination:

the at least one biometric sensor includes at least one of (i) a palm vein sensor and (ii) a ballistocardiography (BCG) sensor;

the at least one biometric sensor includes both a palm vein pattern sensor and a BCG sensor;

the system further includes a data extractor configured to generate a data extraction request in response to a user input, and the authenticator is configured to extract from the memory, upon receipt of the data extraction request from the data extractor, any protected patient data stored therein that the identified user is authorized to access;

the medical device is an endoscope having a shaft extending from a camera head, the medical sensor is an imaging sensor, and the patient data includes images of an internal body cavity of a patient;

the authenticator is at least partially integrated into a medical device;

the authenticator is housed within a camera control unit remotely-located relative to the medical device;

the memory is housed within a camera control unit remotely-located relative to the medical device;

the medical device is an endoscope having a shaft extending from a camera head, and the authenticator is completely integrated into the camera head of the medical device;

the at least one biometric sensor includes a palm vein pattern sensor, and the palm vein pattern sensor includes an infrared (IR) light source configured to emit IR light that penetrates a user's palm, and an IR imager configured to detect IR light reflected back from the user's palm and configured to generate an image therefrom;

the medical device is an endoscope having a shaft extending from a camera head; and the IR imager of the palm vein pattern sensor includes an imaging surface that least partially defines an outer surface of the camera head;

the authenticator is configured to execute an image processing algorithm that maps a shape of palm veins in a closed hand configuration to a shape of palm veins in a stretched hand configuration;

the authenticator is configured to execute an image processing algorithm that maps a shape of palm veins in a stretched hand configuration into a shape of palm veins in a closed hand configuration the at least one biometric sensor includes a BCG sensor, and the BCG sensor includes an accelerometer, a gyroscope, and a processor configured to generate a biometric signal based on respective signals received from the accelerometer and the gyroscope, the biometric signal providing a measure of any repetitive, subtle motions of a user's body caused by a user's beating heart and corresponding shifts to a center of mass of the user's body due to blood flowing therethrough;

the authenticator includes a user profile database configured to store a plurality of user profiles, each including (i) a user ID for a known user of the medical device, and (ii) at least one model of a previously-recorded biometric signal indicative of a biometric characteristic of the known user;

the authenticator includes a comparator configured to compare the at least one biometric signal generated by the at least one biometric sensor with the at least one model of a previously-recorded biometric signal included in the user profiles;

the comparator is configured such that, if the comparator detects a match between the at least one biometric signal generated by the at least one biometric sensor and the at least one model of the previously-recorded biometric signal included in the user profiles, the comparator identifies and authenticates a user as having a user ID belonging to a same user profile as that of a model of a previously-recorded biometric signal that triggered the match;

the comparator is configured such that, if the comparator does not detect a suitable match between the at least one biometric signal generated by the at least one biometric sensor and the at least one model of the previously-recorded biometric signal included in the user profiles, the comparator initiates an enrollment process by which a new user profile is created and saved to the user profile database;

the at least one biometric sensor includes a BCG sensor, and the comparator is configured to analyze images generated by the medical sensor to determine time intervals during which a user held the medical device at least substantially still, and the comparator is configured to consider only portions of a signal that were generated by the BCG sensor during the determined time intervals;

the authenticator is configured to protect the patient data by encrypting the patient data with an encryption key that is unique to a user ID of an identified user;

the authenticator is configured to protect the patient data by saving the patient data to a folder that a user having an identified user ID will be authorized to access and extract;

the authenticator includes a continuity sensor configured to detect interruptions in the use of the medical device, and the authenticator includes a controller configured to protect successive patient data, generated by the medical sensor after an initial identification and authentication of a user, using an identified user ID, until a signal received from the continuity sensor indicates an interruption in the use of the medical device;

the controller is configured to prevent the medical sensor from generating further patient data after receipt of the signal from the continuity sensor indicating the interruption in the use of the medical device, at least until a user begins a subsequent operation of the medical device;

the controller is configured to anonymize patient data generated by the medical sensor after receipt of the signal from the continuity sensor indicating the interruption in the use of the medical device, at least until a user begins a subsequent operation of the medical device;

the controller anonymizes patient data by preventing the patient data from being embedded with patient metadata, and/or removing patient metadata already embedded in the patient data;

the authenticator includes a controller configured to protect successive patient data, generated by the medical sensor after an initial identification and authentication of a user, using an identified user ID, and the controller is configured to create a folder corresponding to a medical procedure and grant read and write access to that folder only to a list of users participating in the medical procedure;

the authenticator includes a controller configured to protect successive patient data, generated by the medical sensor after an initial identification and authentication of a user, using an identified user ID, and the controller is configured to embed in all of the patient data generated during the medical procedure a medical procedure ID indicative of the medical procedure performed by multiple users; and the authenticator includes a controller configured to protect successive patient data, generated by the medical sensor after an initial identification and authentication of a user, using an identified user ID, and the controller is configured to create an access table associated to a medical procedure, the access table listing user IDs of all users allowed to access the data for that medical procedure, and indicating which user ID created each portion of the patient data.

These and other aspects of the present invention will become apparent in light of the drawings and detailed description provided below.

DETAILED DESCRIPTION

The present disclosure describes exemplary embodiments of a system and method for identifying and authenticating a user of a medical device when patient data is generated and stored by the medical device, and when the stored patient data is extracted from the medical device, and for controlling access to the stored patient data without negatively affecting workflow and/or preventing use of the medical device in an emergency situation.

Figure 1:
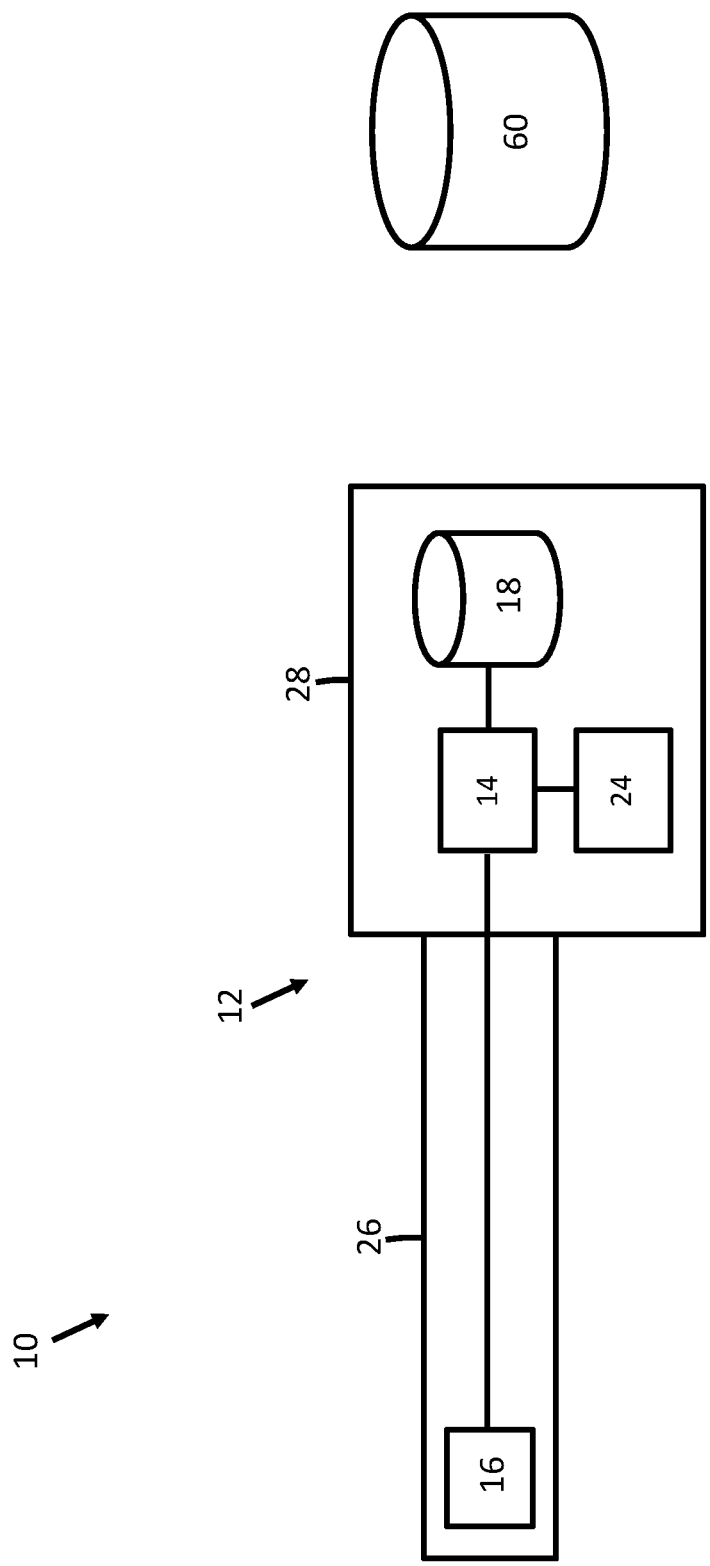
FIG. 1 provides a high level schematic illustration of the present system.
Figure 2:
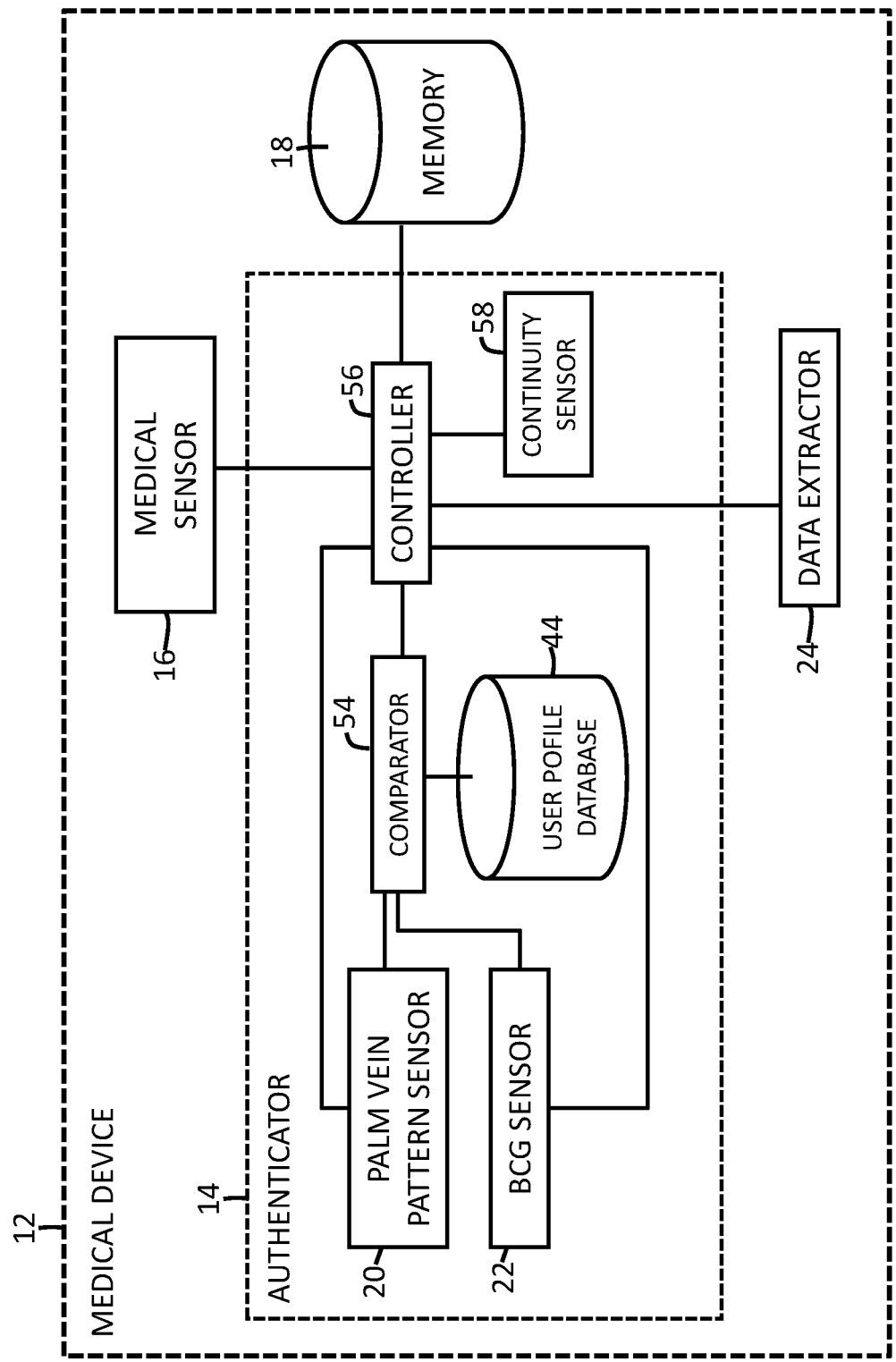
FIG. 2 provides a more detailed schematic illustration of the medical device, authenticator, and data extractor of the system of FIG. 1.

Referring to FIGS. 1 and 2, the system 10 includes a medical device 12 and an authenticator 14. The medical device 12 includes a medical sensor 16 that generates patient data indicative of a sensed physiological characteristic of a patient. The authenticator 14 identifies and authenticates a user of the medical device 12 during operation of the medical device 12, and protects the patient data generated by the medical sensor 16 of the medical device 12 using a user ID unique to the user. The authenticator 14 saves the protected patient data to a memory 18. The authenticator 14 includes at least one biometric sensor 20, 22 configured to generate at least one biometric signal indicative of at least one biometric characteristic of a user of the medical device 12.

In some embodiments, the at least one biometric sensor 20, 22 is one or both of (i) a palm vein pattern sensor 20 configured to generate a biometric signal indicative of a vein pattern of a palm of the user, and (ii) a ballistocardiography (BCG) sensor 22 configured to generate a biometric signal indicative of repetitive, subtle motions of a user's body caused by the user's beating heart and corresponding shifts to a center of mass of the user's body due to blood flowing through the user's body.

In some embodiments, the system 10 further includes a data extractor 24 that generates a data extraction request in response to a user input, and transmits the data extraction request to the authenticator 14. Upon receipt of the data extraction request, the authenticator 14 identifies and authenticates the user of the medical device 12, and extracts from the memory 18 any protected patient data stored therein that the user is authorized to access.

The medical device 12 can be one of various different types of medical instruments. In the illustrated embodiments, the medical device 12 is an endoscope having a shaft 26 (e.g., a flexible shaft, a rigid shaft, etc.) extending from a camera head 28. The medical sensor 16 is an imaging sensor (e.g., a CCD sensor, a CMOS sensor, etc.), and the patient data generated by the imaging sensor includes images of an internal body cavity of a patient. The imaging sensor is positioned at a distal end of the shaft 26, but could alternatively be positioned with in the camera head 28. In some embodiments, the medical device 12 is the same as or similar to known endoscopes manufactured by KARL STORZ GmbH & Co. KG of Tuttlingen, Germany, such as the IMAGE1 S® endoscope. In some embodiments, the medical device 12 is configured for use with known medical systems such as the AIDA® system and/or the OR1 FUSION® system manufactured by KARL STORZ GmbH & Co. KG.

Figure 6:
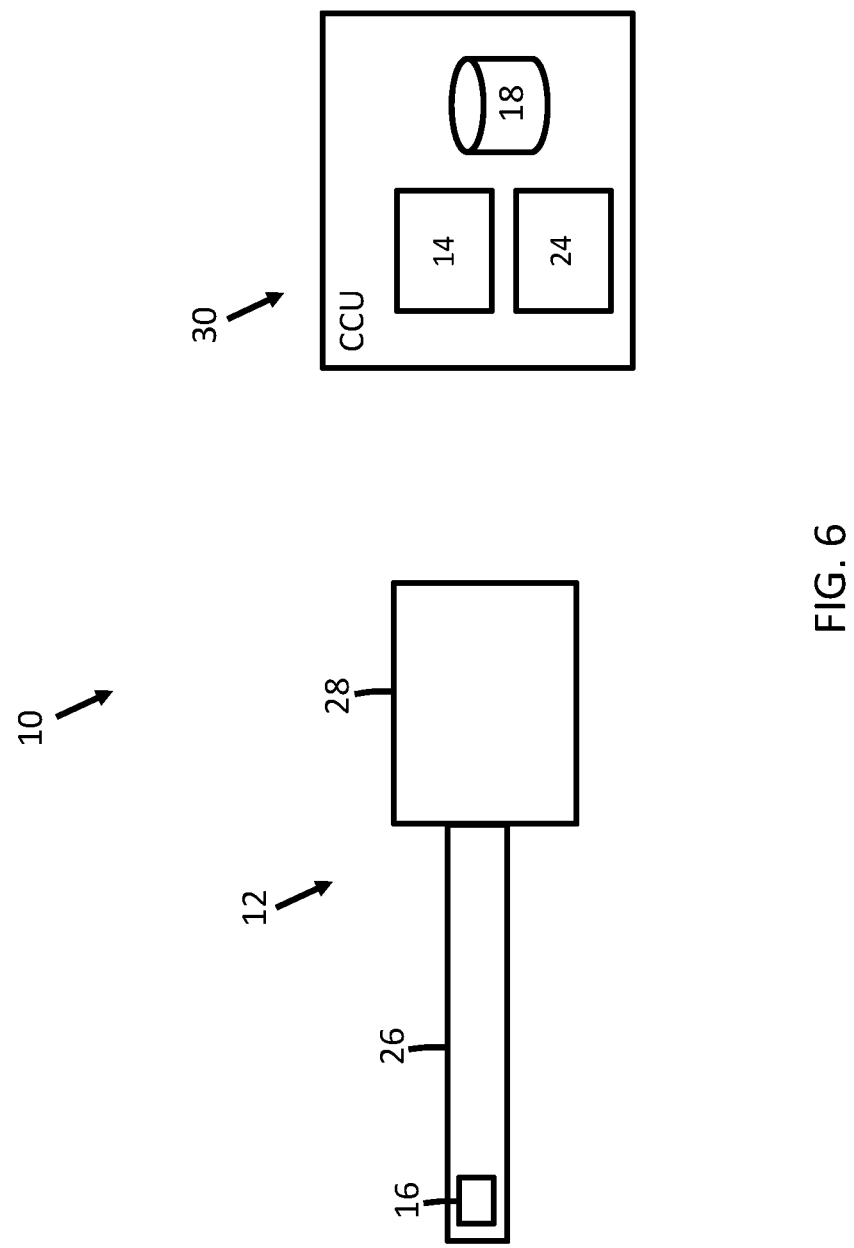
FIG. 6 schematically illustrates another embodiment of the present system.

The authenticator 14 can be at least partially integrated into the medical device 12, or provided as a discrete component relative to the medical device 12. In the embodiment illustrated in FIG. 1, for example, the medical device 12 is an endoscope having a shaft 26 extending from a camera head 28, and the authenticator 14 is completely integrated into the camera head 28, as will be described in more detail below. In the embodiment illustrated in FIG. 6, the authenticator 14 is provided as a discrete component relative to the medical device 12, and is housed within a remotely-located device, in particular a remotely-located camera control unit (CCU) 30. It may be necessary or preferable to provide the authenticator 14 within a remotely-located device when the medical device 12 will be positioned in a hard-to-reach place during the medical procedure, such as when the medical device 12 is a mechanical arm-mounted endoscope that is positioned above an operating table during a medical procedure. In some embodiments, the remotely-located device is another medical device, such as an electro-surgical unit, a scalpel, a suction device, etc. In some embodiments, the system 10 is configured such that the user holds the medical device 12 in one hand while positioning his or her hand relative to the remotely-located device to permit identification and authentication by the authenticator 14. In some embodiments, the medical device 12 separately performs an initial identification of a user via a fingerprint reader or user login interface, and the initial identification is correlated (e.g., at a later time) via the authenticator 14 within the remotely-located device.

The memory 18 can be at least partially integrated into the medical device 12, or provided as a discrete component relative to the medical device 12. In the embodiment illustrated in FIG. 1, for example, the medical device 12 is an endoscope having a shaft 26 extending from a camera head 28, and the memory 18 is completely integrated into the camera head 28. In the embodiment illustrated in FIG. 6, the memory 18 is provided as a discrete component relative to the medical device 12, and is housed within the remotely-located CCU 30.

Referring to FIG. 2, in the illustrated embodiments, the authenticator 14 includes both a palm vein pattern sensor 20 and a BCG sensor 22. In other embodiments, the authenticator 14 includes only a palm vein pattern sensor 20, or only a BCG sensor 22.

Figure 3:
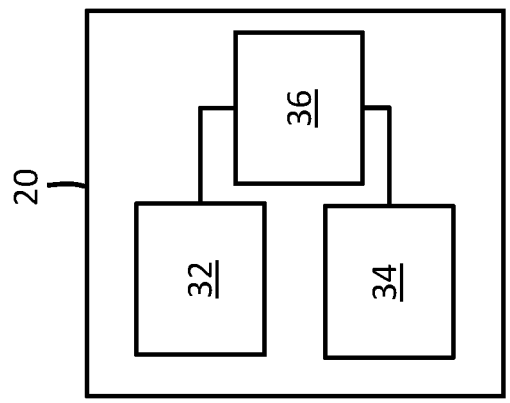
FIG. 3 schematically illustrates the palm vein pattern sensor of the system of FIG. 1.

Referring to FIG. 3, in embodiments in which the authenticator 14 includes a palm vein pattern sensor 20, the palm vein pattern sensor 20 includes an infrared (IR) light source 32 that emits IR light that penetrates a user's palm, an IR imager 34 that detects IR light reflected back from the user's palm and generates an image therefrom, and a processor 36 that controls the IR light source 32 and the IR imager 34 and interfaces with other components of the authenticator 14. The red blood cells present in the user's veins absorb the emitted IR light, causing the veins to appear as black lines in the generated image, while the remainder of the palm appears white in the generated image.

The palm vein pattern sensor 20 is configured to detect a vein pattern of a palm held against or within a predetermined distance (e.g., within a few inches) of the IR imager 34 of the palm vein pattern sensor 20. In some embodiments, the IR imager 34 of the palm vein pattern sensor 20 includes an imaging surface (i.e., a surface configured to receive the IR light reflected back from the user's palm) that is flush with, and/or at least partially defines, an outer surface of a handle portion of the medical device 12. In the embodiment illustrated in FIGS. 1 and 2, for example, the palm vein pattern sensor 20 is embedded within the camera head 28 of the medical device 12 such that an imaging surface of the IR imager 34 of the palm vein pattern sensor 20 partially defines an outer surface of the camera head 28. The palm vein pattern sensor 20 is configured to detect a vein pattern of a user's palm while the user is grasping the camera head 28 (i.e., hereinafter a "closed hand configuration"), and while the user's palm is held within a few inches of the outer surface of the camera head 28 and within a line of sight of the palm vein pattern sensor 20 embedded therein (hereinafter a "stretched hand configuration"). The palm vein pattern sensor 20 is configured to detect a vein pattern of a user's palm regardless of whether the user's palm is bare (i.e., naked) or covered by a medical glove (e.g., a latex glove). In some embodiments, the authenticator 14 is configured to execute an image processing (transformation) algorithm that maps a shape of palm veins in a closed hand configuration into a shape of palm veins in a stretched hand configuration. In some embodiments, the authenticator 14 is additionally or alternatively configured to execute an image processing (transformation) algorithm that maps a shape of palm veins in a stretched hand configuration into a shape of palm veins in a closed hand configuration. This would allow a user to enroll at a workstation with stretched hand, and get identified at the handle portion of the medical device 12 with a closed hand.

Figure 4:
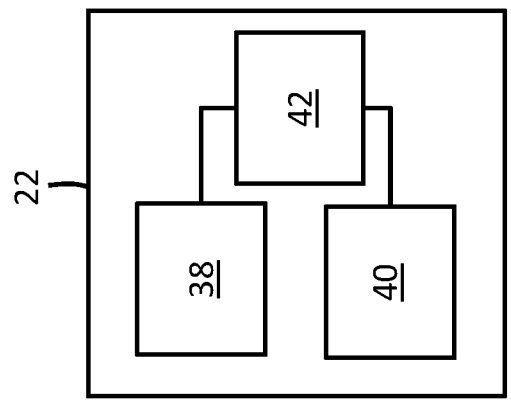
FIG. 4 schematically illustrates the BCG sensor of the system of FIG. 1.

Referring to FIG. 4, in embodiments in which the authenticator 14 includes a BCG sensor 22, the BCG sensor 22 includes an accelerometer 38, a gyroscope 40, and a processor 42 that controls the accelerometer 38 and the gyroscope 40 and interfaces with other components of the authenticator 14. In some embodiments, the accelerometer 38 and gyroscope 40 are the same as or similar to those used in known endoscopic camera heads manufactured by KARL STORZ GmbH & Co. KG of Tuttlingen, Germany, such as the camera head of the IMAGE1 S® endoscope. The processor 42 of the BCG sensor 22 generates a biometric signal (i.e., a BCG signal) based on respective signals received from the accelerometer 38 and the gyroscope 40. The BCG signal provides a measure of repetitive, subtle motions of a user's body caused by the user's beating heart and corresponding shifts to a center of mass of the user's body due to blood flowing through the user's body. The BCG signal is unique to each user, and thus can be used to identify and authenticate a user.

Figure 5:
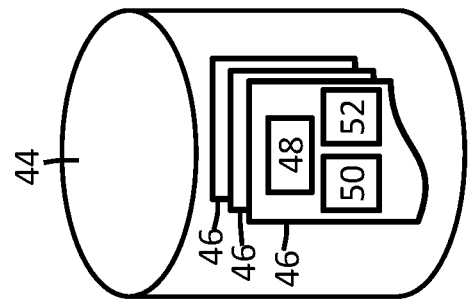
FIG. 5 schematically illustrates the user profile database of the system of FIG. 1.

Referring to FIGS. 2 and 5, in some embodiments, the authenticator 14 includes a user profile database 44 that stores a plurality of user profiles 46. Each of the user profiles 46 includes (i) a user ID 48 (e.g., a name or number) for a known user of the medical device 12, and (ii) at least one model of a previously-recorded biometric signal 50, 52 indicative of a biometric characteristic of the known user. In the illustrated embodiment, the user profiles 46 each include at least one model of a previously-recorded biometric signal 50 generated by the palm vein pattern sensor 20, and at least one model of a previously-recorded biometric signal 52 generated by the BCG sensor 22.

The authenticator 14 includes a comparator 54 that compares the at least one biometric signal generated by the at least one biometric sensor 20, 22 with the at least one model of the previously-recorded biometric signal 50, 52 included in the user profiles 46. If the comparator 54 detects a suitable match, then the comparator 54 identifies and authenticates the user as having the user ID 48 belonging to the same user profile 46 as that of the model of the previously-recorded biometric signal 50, 52 that triggered the match. If the comparator 54 does not detect a suitable match, then the comparator 54 initiates an enrollment process by which a new user profile 46 is created and saved to the user profile database 44. In some embodiments, the authenticator 14 prompts the user to select a user ID 48 (e.g., a name) for the user profile 46 during the enrollment process. In other embodiments, the authenticator 14 automatically assigns the user a user ID 48 (e.g., a unique number) for the user profile 46. The authenticator 14 also collects at least one biometric signal from the at least one biometric sensor 20, 22 and saves the same to the new user profile 46 for future identification. In some embodiments, the authenticator 14 is thus capable of automatically enrolling a user, and thereby avoids the above-described problems associated with devices that require pre-enrollment.

The authenticator 14 also includes a controller 56 that is in communication with, and controls the functionality of, the various components of the authenticator 14. The controller 56 also functions as an interface between components of the authenticator 14 and other components and sub-components of the system 10. During operation of the medical device 12, the controller 56 controls the at least one biometric sensor 20, 22 and the comparator 54 to identify and authenticate the user as described above.

In some embodiments of the present system 10 in which the at least one biometric sensor 20, 22 includes a BCG sensor 22, the controller 56 analyzes images generated by the medical sensor 16 to determine time intervals during which the user is holding the medical device 12 at least substantially still (hereinafter "still time intervals"). Techniques for analyzing images to detect the presence or absence of movement with the image are known. In some embodiments, the controller 56 additionally receives signals from one or more onboard sensors (e.g., accelerometers) and uses such signals in determining the still time intervals. When determining whether there is a suitable match between the BCG signal generated by the BCG sensor 22 and the at least one model of the previously-recorded BCG signals 52 included in the user profiles 46, the controller 56 will only consider portions of the BCG signal that were generated by the medical sensor 16 during the still time intervals. This improves the ability of the controller 56 to accurately identify and authenticate a user via the BCG sensor 22, without requiring the user to purposefully remain still for a certain amount of time (e.g., 10 seconds) for identification.

The controller 56 receives the user ID 48 of the identified user from the comparator 54 (hereinafter the "identified user ID 48"). In some embodiments, the controller 56 protects the patient data by saving the patient data to a folder that the user having the identified user ID 48 will be authorized to access and extract. In other embodiments, the controller 56 protects the patient data received from the medical sensor 16 by encrypting the patient data with an encryption key that is unique to the identified user ID 48, and saving the protected patient data to the memory 18. The patient data can also be embedded with patient metadata providing information such as patient name, date of birth, type of procedure, etc. In some instances, the patient data will by itself constitute PII and/or PHI. In other instances, the patient data will only constitute PII and/or PHI once it is embedded with patient metadata. In general, pictures and videos of internal body cavities are not considered PII or PHI because they cannot be used to identify the patient. However, the patient name, DOB, etc. may be overlaid to pictures and videos thus turning it into PII/PHI.

Referring to FIGS. 1 and 2, in the illustrated embodiment, the authenticator 14 further includes a continuity sensor 58 that aids in detecting interruptions in the use of the medical device 12. In the illustrated embodiments, the continuity sensor 58 is a pressure sensor embedded in the camera head 28 of the medical device 12, and the continuity sensor 58 generates a signal indicative of whether the user is holding the camera head 28. The controller 56 receives the signal from the continuity sensor 58 and uses the signal to detect and verify that the user has been holding the camera head 28 in his or her hand without interruption. This avoids the need for the authenticator 14 to perform repetitive user identification and authentication. After the initial identification and authentication of the user is performed by the authenticator 14, the controller 56 protects each successive patient data generated by the medical sensor 16 by encrypting it as described above, until the signal received from the continuity sensor 58 indicates an interruption in the continuity of user of the medical device 12 (e.g., caused by the user putting down and letting go of the medical device 12 for more than a predetermined period of time).

In some embodiments, the controller 56 is additionally or alternatively configured to operate in standby mode after receipt of a signal from the continuity sensor 58 indicating an interruption, and at least until a user begins a subsequent operation of the medical device 12. In some embodiments, in the standby mode the controller 56 prevents the medical sensor 16 from generating further patient data. In other embodiments, the controller 56 anonymizes the patient data generated by the medical sensor 16 by preventing the patient data from being embedded with patient metadata, and/or removing patient metadata already embedded in the patient data. In some embodiments, the system 10 is configured to permit a user to selectively change between one or more of these standby mode functions of the controller 56. This permits an administrator to set the system 10 to work in the manner preferred by the particular hospital or medical facility.

Referring again to FIG. 1, in the illustrated embodiment, the system 10 further includes a remote server 60 (e.g., a DICOM server) that is in communication with the authenticator 14, and from which the authenticator 14 receives procedure data indicative of the medical procedure being performed with the medical device 12 (e.g., indicative of the type of medical procedure, the expected duration of the medical procedure, the number of users expected to use the medical device 12 during the medical procedure, the identity of the users expected to use the medical device 12 during the medical procedure, etc.).

In some embodiments in which the procedure data indicates that multiple users will be handling the medical device 12 during the medical procedure, the controller 56 of the authenticator 14 protects each portion of the patient data so that it is only accessible by the respective user who handled the medical device when that portion of the patient data was generated, and/or another authorized user.

In some embodiments, the controller 56 creates a folder corresponding to the medical procedure and grants read and write access to that folder to the list of users participating in the medical procedure, so that all of these users—and only these users—can create and access the data. In some embodiments, the controller 56 also embeds in all of the patient data generated during the medical procedure a medical procedure ID indicative of the medical procedure performed by the multiple users. The authenticator 14 will authorize all of the users who participated in the medical procedure to access the patient data protected with that medical procedure ID.

In some embodiments, the controller 56 additionally or alternatively creates an access table associated to the medical procedure, the access table listing the user ID of all users allowed to access the data for that medical procedure. The access table can also indicate which user ID created each portion of the patient data. When a user requests access to a particular portion of the patent data that he or she did not create, the controller 56 will look at the access table to determine if that user is authorized to access the patent data, and then it will make it available to the user, decrypting it, if necessary using the other user ID (the one who created the patient data). The access table can be stored in a secure memory area of the device that is not accessible by regular users.

In some embodiments of the present system 10 in which the at least one biometric sensor 20, 22 includes a BCG sensor 22, procedure data received from the remote server 60 is used by the comparator 54 to predict the posture of the user and thereby select an appropriate posture-dependent user model. The posture of a user (e.g., a surgeon) is very predictable based on the type of medical procedure being performed, and thus information regarding the medical procedure being performed is used by the comparator 54 to pre-select the posture-dependent user model.

The functionality of various components and sub-components of the system 10 can be implemented using analog and/or digital hardware (e.g., counters, switches, logic devices, memory devices, programmable processors, non-transitory computer-readable storage mediums), software, firmware, or a combination thereof. The various components and sub-components of the system 10 can be specially constructed to perform the desired functionality, and/or can include one or more general purpose computers selectively configured to perform the desired functionality. In some embodiments, the functionality described herein can be performed by executing software, which can be stored, for example, on a non-transitory computer-readable storage medium. In view of the present disclosure, a person having ordinary skill in the art would be able to adapt (e.g., construct, program) the various components and sub-components of the system 10 to perform the functionality described herein without undue experimentation.

Although the components and sub-components of the system 10 are described as being discrete components separate from one another, in some embodiments one or more of those components can be combined into a single component. For example, although the authenticator 14 is described as being a discrete component separate from the medical device 12, in some embodiments one or more components or functions of the authenticator 14 can be a component or function of the medical device 12, or vice versa. Similarly, although the data extractor 24 is described as being a discrete component separate from the medical device 12 and the authenticator 14, in some embodiments one or more components or functions of the data extractor 24 can be a component or function of the medical device 12 or the authenticator 14, or vice versa.

The various connections between the components of the system 10 can include wired and/or wireless connections. Wired connections can be made by any type of conductive transmission line. In some embodiments, one or more components of the system 10 can be connected via a network connection (e.g., via the Internet and/or via a personal area network (PAN), a local area network (LAN), a wide area network (WAN), etc.).

Another aspect of the present invention involves a method that includes the steps of: (i) generating patient data using a medical device, the patient data indicative of a sensed physiological characteristic of a patient; (ii) identifying and authenticating a user of the medical device based on at least one biometric signal generated by at least one biometric sensor; (iii) protecting patient data generated by the medical device using a user ID unique to the user identified during the identifying and authenticating step; and (iv) saving the protected patient data to a memory.

As will be apparent in view of the above-described functionality of the system 10 and the various components thereof, the steps of the method can include various sub-steps, and/or various other steps in addition to the above-described steps. Although the steps of the method are set forth in a particular order using numeric and/or alphanumeric labels, the labels are used merely for convenient identification of steps, and are not intended to imply, specify, or require a particular order of carrying out such steps. Furthermore, in some embodiments, the method can include more or less steps than those discussed herein.

The terms "controlling," "determining," "identifying," "analyzing," and variations thereof, are each used herein to refer to one or more actions and/or processes that can be implemented, for example, via a programmable processor or similar electronic computing device by manipulating and/or transforming data within the programmable processor's memory into other data within the programmable processor's memory.

The present disclosure describes aspects of the present invention with reference to the exemplary embodiments illustrated in the drawings; however, aspects of the present invention are not limited to the exemplary embodiments illustrated in the drawings. It will be apparent to those of ordinary skill in the art that aspects of the present invention include many more embodiments. Accordingly, aspects of the present invention are not to be restricted in light of the exemplary embodiments illustrated in the drawings. It will also be apparent to those of ordinary skill in the art that variations and modifications can be made without departing from the true scope of the present disclosure. For example, in some instances, one or more features disclosed in connection with one embodiment can be used alone or in combination with one or more features of one or more other embodiments.

What is claimed is:

1. A system, comprising:
   an endoscope having a medical sensor configured to generate patient data indicative of a sensed physiological characteristic of a patient; and
   an authenticator having at least one biometric sensor configured to generate at least one biometric signal indicative of at least one biometric characteristic of a user of the endoscope, the at least one biometric sensor including a palm vein sensor and a ballistocardiography (BCG) sensor;
   the authenticator configured to (i) identify and authenticate a user of the endoscope, (ii) protect patient data generated by the medical sensor of the endoscope using a user ID unique to the identified user, and (iii) save the protected patient data to a memory.

2. The system of claim 1, further comprising a data extractor configured to generate a data extraction request in response to a user input; and
   wherein the authenticator is configured to extract from the memory, upon receipt of the data extraction request from the data extractor, any protected patient data stored therein that the identified user is authorized to access.

3. The system of claim 1, wherein the endoscope includes a shaft extending from a camera head, the medical sensor is an imaging sensor, and the patient data includes images of an internal body cavity of a patient.

4. The system of claim 1, wherein the authenticator is at least partially integrated into the endoscope.

5. The system of claim 4, wherein the authenticator is housed within a camera control unit remotely-located relative to the endoscope.

6. The system of claim 4, wherein the memory is housed within a camera control unit remotely-located relative to the endoscope.

7. The system of claim 4, wherein the endoscope includes a shaft extending from a camera head; and
   wherein the authenticator is completely integrated into the camera head of the endoscope.

8. The system of claim 1, wherein the BCG sensor includes an accelerometer, a gyroscope, and a processor configured to generate a biometric signal based on respective signals received from the accelerometer and the gyroscope, the biometric signal providing a measure of any repetitive, subtle motions of a user's body caused by a user's beating heart and corresponding shifts to a center of mass of the user's body due to blood flowing therethrough.

9. The system of claim 1, wherein the authenticator includes a user profile database configured to store a plurality of user profiles, each including (i) a user ID for a known user of the endoscope, and (ii) at least one model of a previously-recorded biometric signal indicative of a biometric characteristic of the known user.

10. The system of claim 9, wherein the authenticator includes a comparator configured to compare the at least one biometric signal generated by the at least one biometric sensor with the at least one model of a previously-recorded biometric signal included in the user profiles.

11. The system of claim 10, wherein the comparator is configured such that, if the comparator detects a match between the at least one biometric signal generated by the at least one biometric sensor and the at least one model of the previously-recorded biometric signal included in the user profiles, the comparator identifies and authenticates a user as having a user ID belonging to a same user profile as that of a model of a previously-recorded biometric signal that triggered the match.

12. The system of claim 10, wherein the comparator is configured such that, if the comparator does not detect a suitable match between the at least one biometric signal generated by the at least one biometric sensor and the at least one model of the previously-recorded biometric signal included in the user profiles, the comparator initiates an enrollment process by which a new user profile is created and saved to the user profile database.

13. The system of claim 1, wherein the authenticator is configured to protect the patient data by encrypting the patient data with an encryption key that is unique to a user ID of an identified user.

14. The system of claim 1, wherein the authenticator is configured to protect the patient data by saving the patient data to a folder that a user having an identified user ID will be authorized to access and extract.

15. The system of claim 1, wherein the authenticator includes a controller configured to protect successive patient data, generated by the medical sensor after an initial identification and authentication of a user, using an identified user ID; and
wherein the controller is configured to create a folder corresponding to a medical procedure and grant read and write access to that folder only to a list of users participating in the medical procedure.

16. The system of claim 1, wherein the authenticator includes a controller configured to protect successive patient data, generated by the medical sensor after an initial identification and authentication of a user, using an identified user ID; and
wherein the controller is configured to embed in all of the patient data generated during a medical procedure a medical procedure ID indicative of the medical procedure performed by multiple users.

17. The system of claim 1, wherein the authenticator includes a controller configured to protect successive patient data, generated by the medical sensor after an initial identification and authentication of a user, using an identified user ID; and
wherein the controller is configured to create an access table associated to a medical procedure, the access table listing user IDs of all users allowed to access the data for that medical procedure, and indicating which user ID created each portion of the patient data.

18. A system, comprising:
an endoscope having a medical sensor configured to generate patient data indicative of a sensed physiological characteristic of a patient; and
an authenticator having at least one biometric sensor configured to generate at least one biometric signal indicative of at least one biometric characteristic of a user of the endoscope, the at least one biometric sensor including a palm vein sensor having an infrared (IR) light source configured to emit IR light that penetrates a user's palm, and an IR imager configured to detect IR light reflected back from the user's palm and configured to generate an image therefrom;
the authenticator configured to (i) identify and authenticate a user of the endoscope, (ii) protect patient data generated by the medical sensor of the endoscope using a user ID unique to the identified user, and (iii) save the protected patient data to a memory;
wherein the endoscope includes a shaft extending from a camera head; and
wherein the IR imager of the palm vein sensor includes an imaging surface that least partially defines an outer surface of the camera head; and
wherein the authenticator is configured to execute an image processing algorithm that maps a shape of palm veins in a closed hand configuration to a shape of palm veins in a stretched hand configuration.

19. The system of claim 18, wherein the medical sensor is an imaging sensor, and the patient data includes images of an internal body cavity of a patient.

20. The system of claim 18, wherein the authenticator is completely integrated into the camera head of the endoscope.

21. A system, comprising:
an endoscope having a medical sensor configured to generate patient data indicative of a sensed physiological characteristic of a patient; and
an authenticator having at least one biometric sensor configured to generate at least one biometric signal indicative of at least one biometric characteristic of a user of the endoscope, the at least one biometric sensor including a ballistocardiography (BCG) sensor;
the authenticator configured to (i) identify and authenticate a user of the endoscope, (ii) protect patient data generated by the medical sensor of the endoscope using a user ID unique to the identified user, and (iii) save the protected patient data to a memory;
wherein the authenticator includes a user profile database configured to store a plurality of user profiles, each including (i) a user ID for a known user of the endoscope, and (ii) at least one model of a previously-recorded biometric signal indicative of a biometric characteristic of the known user;
wherein the authenticator includes a comparator configured to compare a biometric signal generated by the BCG sensor with the at least one model of a previously-recorded biometric signal included in the user profiles;
wherein the comparator is configured to analyze images generated by the medical sensor to determine time intervals during which a user held the endoscope at least substantially still; and
wherein the comparator is configured to consider only portions of the biometric signal that were generated by the BCG sensor during the determined time intervals.

22. The system of claim 21, wherein the BCG sensor includes an accelerometer, a gyroscope, and a processor configured to generate the biometric signal of the BCG sensor based on respective signals received from the accelerometer and the gyroscope, the biometric signal providing a measure of any repetitive, subtle motions of a user's body caused by a user's beating heart and corresponding shifts to a center of mass of the user's body due to blood flowing therethrough.

23. A system, comprising:
an endoscope having a medical sensor configured to generate patient data indicative of a sensed physiological characteristic of a patient; and
an authenticator having at least one biometric sensor configured to generate at least one biometric signal indicative of at least one biometric characteristic of a user of the endoscope, the at least one biometric sensor including at least one of (i) a palm vein sensor and (ii) a ballistocardiography (BCG) sensor;
the authenticator configured to (i) identify and authenticate a user of the endoscope, (ii) protect patient data generated by the medical sensor of the endoscope using a user ID unique to the identified user, and (iii) save the protected patient data to a memory;

wherein the endoscope includes a shaft extending from a camera head;

wherein the authenticator includes a continuity sensor configured to detect interruptions in the use of the endoscope;

wherein the continuity sensor is a pressure sensor in the camera head;

wherein the continuity sensor generates a signal indicative of whether the user is holding the camera head; and wherein the authenticator includes a controller configured to protect successive patient data, generated by the medical sensor after an initial identification and authentication of a user, using an identified user ID, until a signal received from the continuity sensor indicates an interruption in the use of the endoscope.

24. The system of claim 23, wherein the controller is configured to prevent the medical sensor from generating further patient data after receipt of the signal from the continuity sensor indicating the interruption in the use of the endoscope, at least until a user begins a subsequent operation of the endoscope.

25. The system of claim 23, wherein the controller is configured to anonymize patient data generated by the medical sensor after receipt of the signal from the continuity sensor indicating the interruption in the use of the endoscope, at least until a user begins a subsequent operation of the endoscope.

26. The system of claim 25, wherein the controller anonymizes patient data by preventing the patient data from being embedded with patient metadata, and/or removing patient metadata already embedded in the patient data.

* * * * *